United States Patent [19]

Arnold et al.

[11] Patent Number: 5,560,358
[45] Date of Patent: Oct. 1, 1996

[54] CONNECTOR DESIGN FOR MULTI-CONTACT MEDICAL ELECTRODE

[75] Inventors: Michael A. Arnold, Woburn; Eric R. Cosman, Belmont; William A. Chiklakis, Georgetown, all of Mass.

[73] Assignee: Radionics, Inc., Burlington, Mass.

[21] Appl. No.: 303,022

[22] Filed: Sep. 8, 1994

[51] Int. Cl.⁶ .................................................. A61B 5/04
[52] U.S. Cl. ...................... 128/642; 439/783; 439/864; 439/909
[58] Field of Search ...................... 128/642, 639, 128/640, 644; 607/37, 116, 117, 122, 148; 439/783, 790, 838, 864, 909

[56] References Cited

U.S. PATENT DOCUMENTS

| | | | |
|---|---|---|---|
| 3,372,367 | 3/1968 | Concannon | 439/864 |
| 3,824,529 | 7/1974 | Dorrell | 439/864 |
| 4,245,642 | 1/1981 | Skubitz et al. | 607/37 |
| 4,840,580 | 6/1989 | Saell et al. | 439/783 |
| 4,869,255 | 9/1989 | Putz | 128/642 |

FOREIGN PATENT DOCUMENTS 112072  5/1991  Japan ..................... 439/838

Primary Examiner—Lee S. Cohen
Attorney, Agent, or Firm—Richard J. Birch

[57] ABSTRACT

An electrical brain contact device and device for connecting a plurality of lead wires with individual take-up terminals is described. The lead wires in the brain contact device extend to a terminal mount with an array of lead-wire terminals on it. A connector assembly includes a connector block with a matching array of take-up terminals and an elongate cavity to receive the terminal mount, and a mechanism to removably draw the take-up terminals into terminal-to-terminal contact with the terminal mount to facilitate electrical connection.

4 Claims, 4 Drawing Sheets

CONNECTOR DESIGN FOR MULTI-CONTACT MEDICAL ELECTRODE

BACKGROUND TO THE INVENTION

The use of multi-contact recording electrodes for measuring brain electrical activity of epileptic patients has been carried out for many years. These electrodes can be of various shapes and types. Two especially common designs are the surface or cortical design, which are flat electrodes to lay on the surface of the brain, and depth electrodes, which are slender cylindrical structures that can be implanted directly into the mass of the brain. In both of these electrodes, multiple contacts are used to record the activity at several sites in the brain simultaneously so as to try to determine the focus of the epileptic seizure in the patient's brain.

A long-standing problem with such multi-contact electrodes is a simple but reliable external connection means to external monitoring apparatus. Typically, the electrode will have a lead cable or tubing which carries several lead wires from the brain electrical contacts externally to a terminal mount. The terminal mount, in turn, will be connected via a second cable to external monitoring apparatus such as an EEG monitor. The terminal mount on the electrode should preferentially be very narrow so that it can be tunneled underneath the patient's skin from the incision site to an external exit site. This tunneling process is used typically to minimize the chance of migratory bacteria directly entering the surgical wound. Thus, it is desired that the terminal mount on the electrode be very narrow so that it can be tunneled under the skin by passing it through a hypodermic needle which has already been inserted through the skin tunnel.

A particularly useful design for the terminal mount is a configuration which utilizes a linear array of concentric terminal rings mounted on tubular sheathing. This terminal mount design has been adapted for use with several different styles of connector assemblies. For example, Putz (U.S. Pat. No. 4,850,359) describes a connector comprised of two blocks or pieces with a space or major groove between them, the space or groove being designed to accept the linear array of conductors of the electrode's terminal mount. The groove or space includes take-up terminals arranged in a linear array. The electrode terminal mount is positioned into the space or groove, and the two connector blocks or pieces are clamped or brought together to assure electrical contact between the electrode terminal mount conductor array and the array of take-up terminals located within the space between the two blocks or pieces of the connector means. Another connector assembly described by Putz (U.S. Pat. No. 4,869,255) is a connector block with an elongate cavity to hold the electrode terminal mount, and an array of intersecting perpendicular holes. The cavity and the holes are described as being a first and a second space within the connector block. An additional piece or element is taught in this Putz patent and is referred to as a conductor support. The conductor support holds an array of mating conductor pins. To make an electrical connection, the array of pins on the conductor support is inserted into the matching array of holes on the connector block. As the array of pins enters the cavity, or first space into which the terminal mount electrode array has been inserted, the pins push into contact with the terminal mount array, thereby making electrical connection with the terminal mount array. Each of the designs described above by Putz involves connector assemblies with two or more separable pieces. Since a surgeon may use up to eight or ten electrodes per patient, the likelihood of losing or dropping one of these connector pieces in the operating room, rendering it non-sterile, presents a particular problem. In addition, the complexity of assembly of these connector parts can make the assembly quite time consuming, which also is a deficit in a busy operating room. Furthermore, the designs of Putz have geometric and physical complexities. For example, the use of two blocks with a space between them and the action of moving the blocks together so as to more the take-up terminals into contact with the electrodes terminal mount array involves a complex of pieces, holding elements, and conductor arrays with potentially difficult to control forces on the conductor arrays and resulting variability of array contact and possible unwanted distortion of the terminal mount array conductors. As another example, in the Putz patent, the use of first and second spaces in the connector block with an additional conductor support element, having conductors such as pins, to be inserted into the second spaces so as to move into the first space and therein to forcibly contact and distort the conductor array of the electrode terminal mount, poses a complex geometry, criticality of tolerances of many parts, potential overstress and overdistortion of the terminal mount's conductor array, resulting variability of electrical contact, etc.

The present invention involves a different and novel approach to this multi-electrode connection problem. It provides a connector assembly design which is extremely easy to use, yet provides reliable electrical connections and unique and simple geometry and action.

Among the objects of the present invention, without limitation to its scope and novelty, include:

A simplified connector block with fewer separable elements and/or simpler geometry;

A design which does not require two block-like elements to close down on a space between them, and in turn pushes upon connector contact arrays so as to contact electrode contact arrays within said space;

A design which does not require two communicating spaces in the connector block with a connector support element or conductive elements to be moved into the second space so as to squeeze on a connector array or electrode array in the first space;

A design which has, in one embodiment, a single cavity in the connector block into which the terminal array can be inserted, and a spring-loaded connector contact array within said cavity, and having an actuator means within said cavity to hold said spring-loaded array open so that said terminal array can be inserted into said cavity without contacting said spring-loaded array, and then said actuator means can cause said spring-loaded array to close or to release upon said terminal array so as to put predictable and/or proper pressure of contact on or between said two arrays for superior reliability and durability.

DESCRIPTION OF THE INVENTION

The drawings described below illustrate various embodiments of the present invention including a connector design for a multi-contact medical electrode. They illustrate the use with depth electrode devices and cortical surface electrode devices. The illustrations are examples of the invention and are not meant to limit the scope of the invention's claims or to limit variations of the claimed inventions which are possible to design by those skilled in the art.

Figure 1:
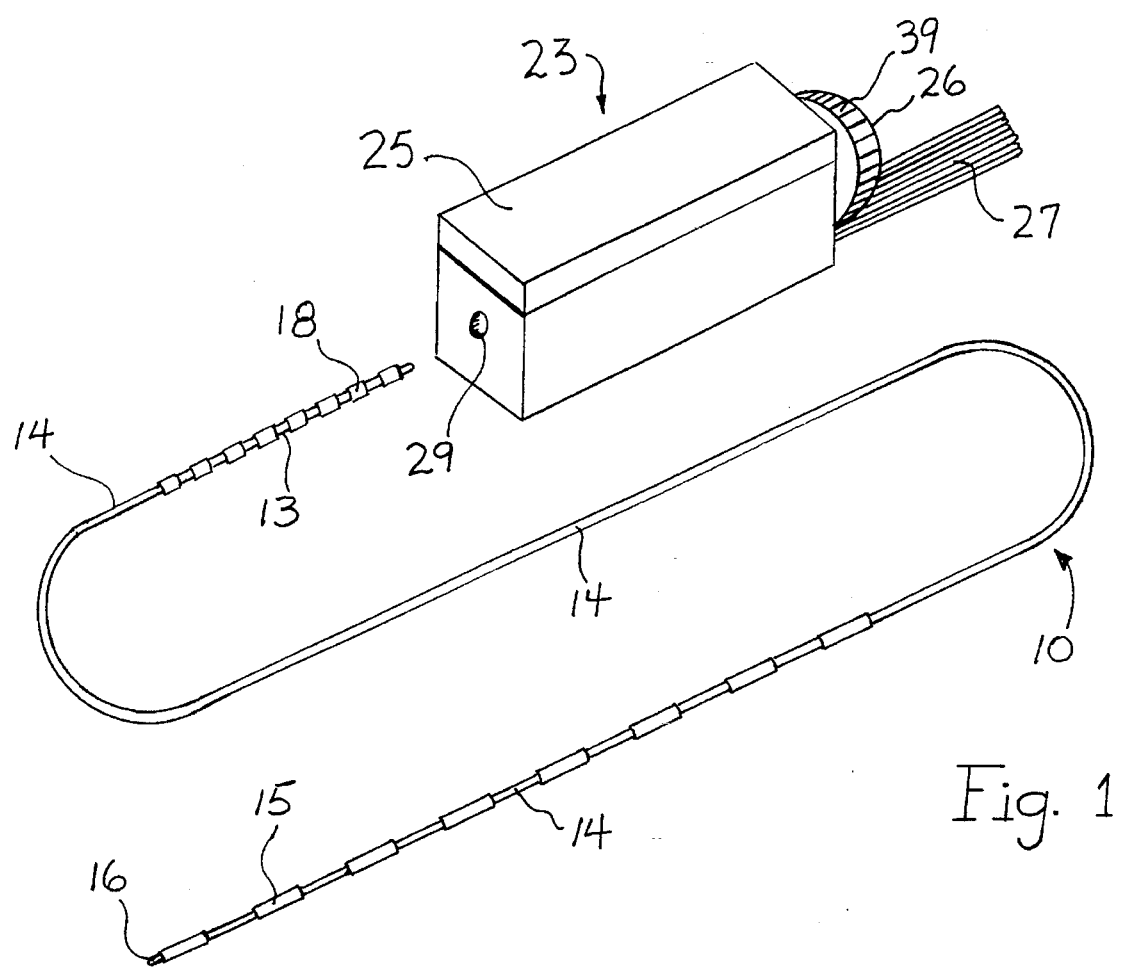
FIG. 1 shows an embodiment of the present invention with a depth electrode terminal contact array, and connector assembly in perspective view.
Figure 7:
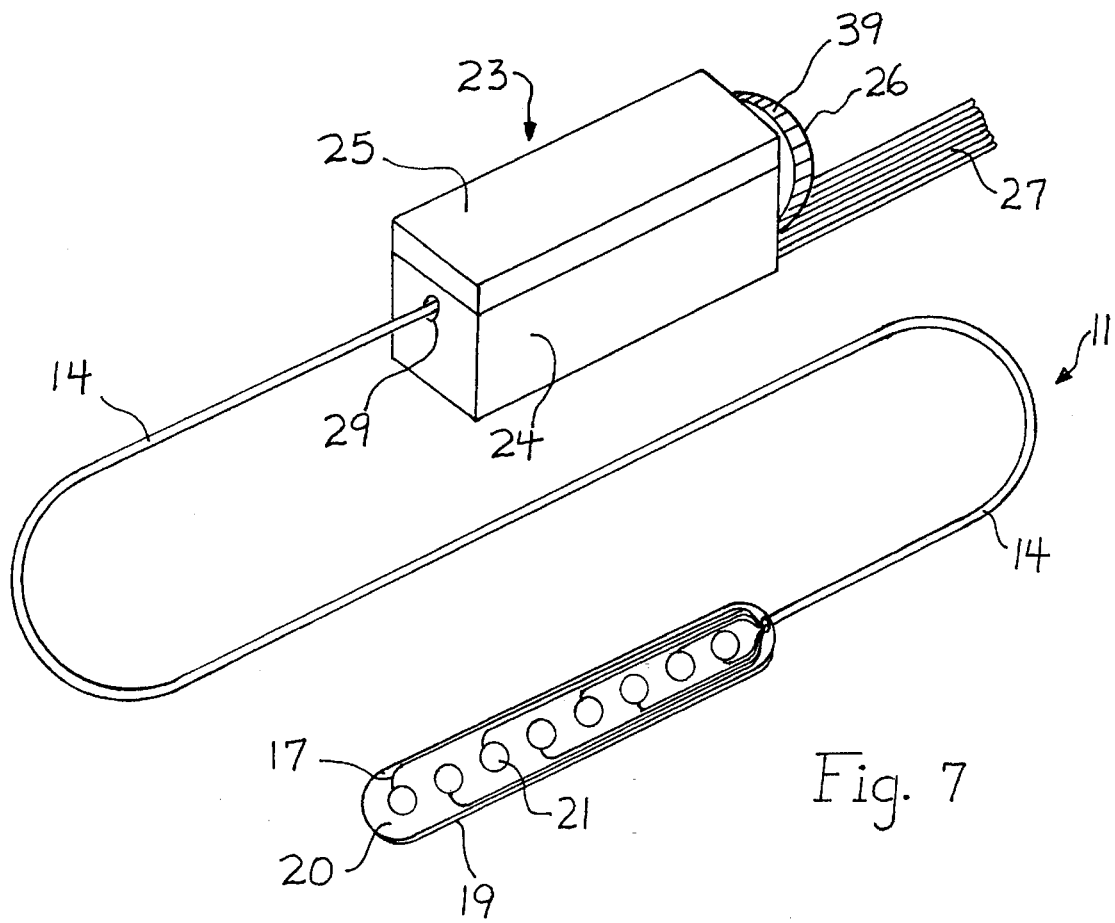
FIG. 7 is a perspective view of a cortical surface electrode device in accordance with this invention.

Two patient-contacting electrode devices are illustrated, including a depth electrode device 10, indicated by the assembly of cylindrical linear contacts, shown in FIG. 1, and a cortical surface electrode device 11, indicated by the flattened surface contact linear electrode array, shown in FIG. 7. Patient contact electrode systems devices 10 and 11 can be coupled to an identical connector assembly 23, as shown in FIGS. 1 and 7, in accordance with this invention.

Figure 2:
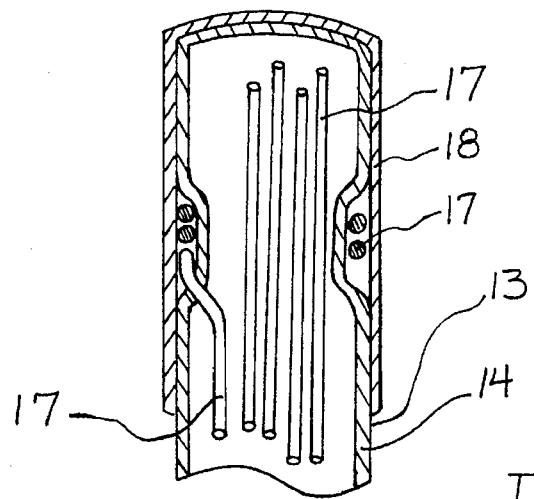
FIG. 2 is an enlarged fragmentary sectional view of the depth electrode shown in FIG. 1.
Figure 3:
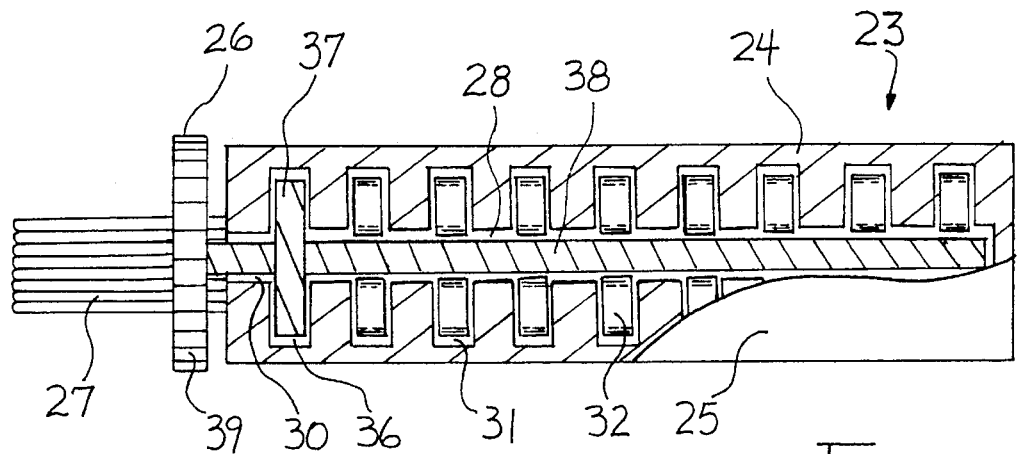
FIG. 3 is a partially cut-away plan view of the connector assembly of FIG. 1.
Figure 4:
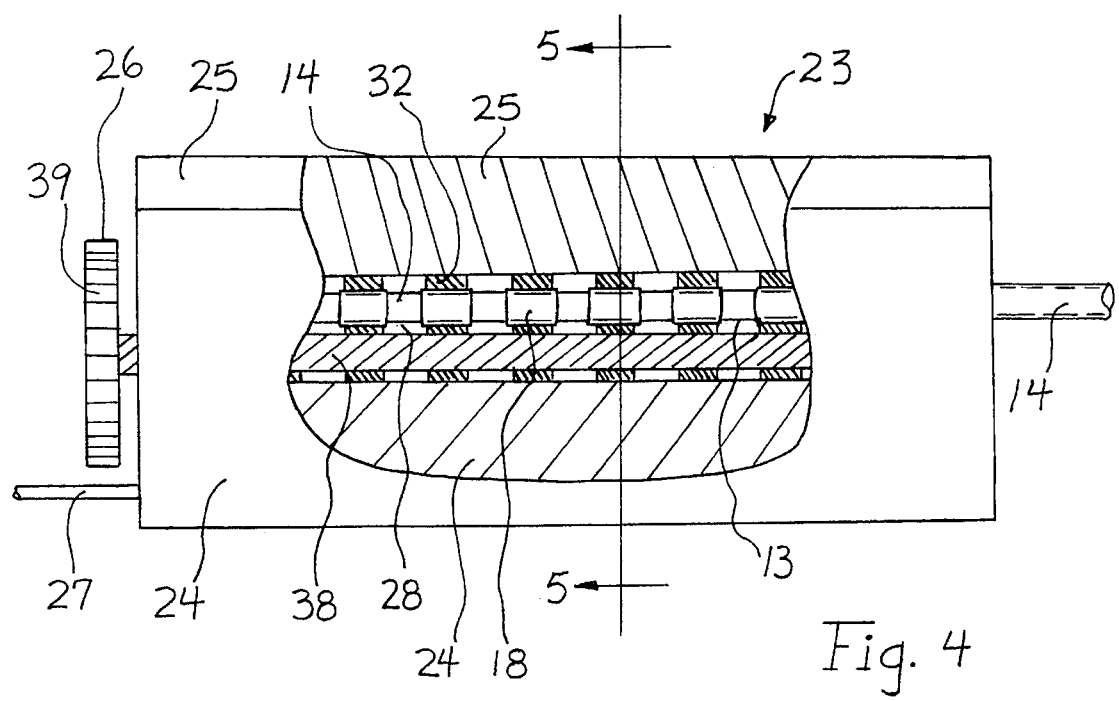
FIG. 4 is a partially cut-away side-elevation view of the connector assembly of FIGS. 1 and 3, with the terminal mount inserted into the connector assembly.

Devices 10 and 11 all include identical terminal mounts 13, shown in FIGS. 1, 2, and 4–6. The details of the terminal mounts 13 are shown in FIGS. 1 and 2.

Referring to FIGS. 1, 2, 4, 5, and 6, depth electrode 10 includes a non-conductive, hollow, flexible tubing 14 having electrode rings 15 spaced along it and attached to it. Hollow tubing 14 has a closed distal termination 16. Individual lead wires 17 extend inside hollow tubing 14 from each electrode ring 15 in a direction away from closed distal termination 16 and projecting to the terminal mount 13. At the terminal mount 13, the lead wires 17 are connected to lead wire terminal rings 18, which form a part of the terminal mount 13. The series of rings 18 in this particular example for a linear electrode contact array as part of the terminal mount. Other geometries of terminal mount contact arrays could obviously be designed. Depth electrode 10 is of a type known in the prior art.

Referring to FIGS. 7, 2, 4, 5, and 6, the cortical surface electrode device 11 includes a distal strip assembly 19. The strip assembly 19 has a flexible sheeting member 20 which incorporates a number of flat electrode discs 21, coplanar with flexible sheeting 20. Electrode discs 21 may be held in flexible sheeting 20 by being placed between its two bonded layers. Individual lead wires 17 are connected with each electrode disc 21, and are projected through hollow tubing 14 to the terminal mount 13. Cortical surface electrode 11 itself is of a type known in the prior art.

In each of the two embodiments, terminal mount 13 includes hollow tubing 14 which forms a base for mounting lead wire terminal rings 18. Lead wires 17 extend through the hollow tubing 14 in the manner shown in FIG. 2, with each lead wire 17 attached to one lead wire terminal ring 18.

The hollow tubing 14 is preferably made of a non-conductive flexible material such as polyurethane. Other suitable materials are available for this application and include silicone elastomer material.

The flexible sheeting 20 used in the cortical surface electrode 11 may be made from a silicone elastomer material.

As illustrated in FIGS. 1, 3, 4, 5, 6, and 7, each of the illustrated brain contact devices has a terminal mount 13 which can be attached to a connector assembly 23. Connector assembly 23 includes a connector block 24, a transparent top plate 25, a cam 26, and outlet wires 27 which extend to provide a connection with monitoring equipment. The connector block 24 and the top plate 25 may be permanently joined together, and together form a unitized connector housing inside of which is a single elongated cavity 28. The elongated cavity 28 is joined to an axial opening 29 at one end of the connector block 24. The elongated cavity 28 extends to the opposite end of the connector block, terminating in a slotted opening 30 in which the cam 26 is positioned.

The cavity 28 within the connector block 24 has an array of terminal recesses 31 each of which restrains and/or holds a take-up terminal 32. Each take-up terminal 32 may be constructed of gold-plated steel sheeting since such a material has excellent characteristics for contact reliability and electrical conductivity. Each take-up terminal 32 has a flat, flexible arm 33 which is also within the elongate cavity 28. The other end of the take-up terminal 32 is a terminal lead 34 which extends through the connector block 24 and terminates in the outlet wire element 35. In the outlet wire element 35, the take-up terminal 32 is connected to the appropriate outlet wire 27. The outlet wire element 35 may be a filled volume or stratum of non-conductive material such as insulative epoxy or glue. The outlet wires 27 exit the connector assembly 23 and provide a means to connect to external monitoring equipment.

Figure 5:
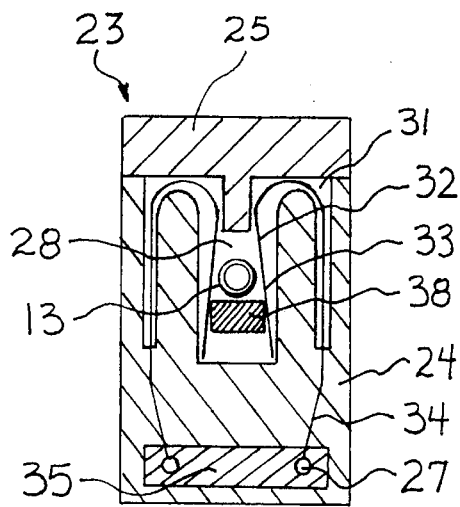
FIG. 5 is an end sectional view of the device of FIG. 4 in an electrically unconnected condition, taken along section 5—5, as indicated in FIG. 4.
Figure 6:
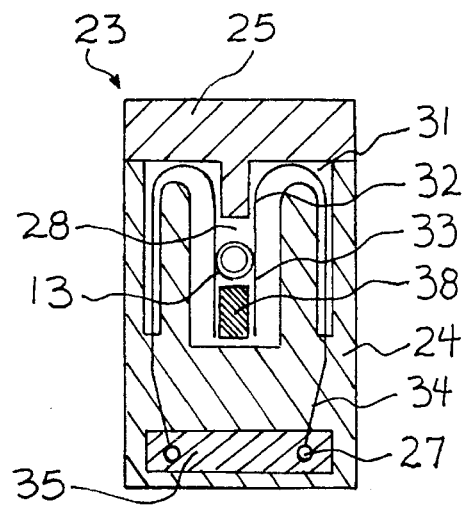
FIG. 6 is an end sectional view of the device of FIG. 5 in an electrically connected condition.

The cam 26 enters the connector assembly 23 through a slotted opening 30. The connector block 24 has a cam lock recess 36 which holds the cam lock 37. The entrapment of cam lock 37 within cam lock recess 36 prevents any longitudinal movement of the cam 26. A cam shaft 38 projects from the cam lock 37 through the elongate cavity 28 to the opposite end of the connector block 24. Outside the connector block 24 the cam 26 terminates with a cam wheel 39. The cam wheel 39 can be rotated easily by digital manipulation, which provides rotation of the internal cam shaft 38. In FIGS. 5 and 6 is illustrated a cross-sectional view of the connector assembly 23. In cross-sectional view, the cam shaft 38 is shown as substantially rectangular in shape, with one side substantially longer than the other. The cam 26 may be constructed of a rugged non-conductive material such as a tough plastic.

FIG. 5 illustrates an end sectional view of the connector assembly 23 and the terminal mount 13 in an electrically unconnected condition, meaning that the electrode terminal array of contacts are not in forcible electrical contact with the connector's take-up terminal array. The cam shaft 38 in this situation is in the horizontal position, holding each pair of take-up terminals 32 in the most separated condition. In this position the terminal mount 13 may be inserted or withdrawn from the connector assembly 23 freely.

FIG. 6 illustrates an end sectional view of the connector assembly 23 and the terminal mount 13 in an electrically connected condition, meaning that the two contact arrays are in forced electrical contact. The cam shaft 38 in this situation has been rotated 90° from its position as shown in FIG. 5. Now the cam shaft 38 is in the vertical position which releases the separative restraint on the take-up terminals 32, allowing the take-up terminals to come together under their own spring-loaded condition, thereby allowing them to make forcible electrical contact rings 18 of the terminal mount array structure 13. In this position the terminal mount 13 is held inside the connector assembly 23 by mechanical interference, and a good electrical connection has been made.

Figure 8A:
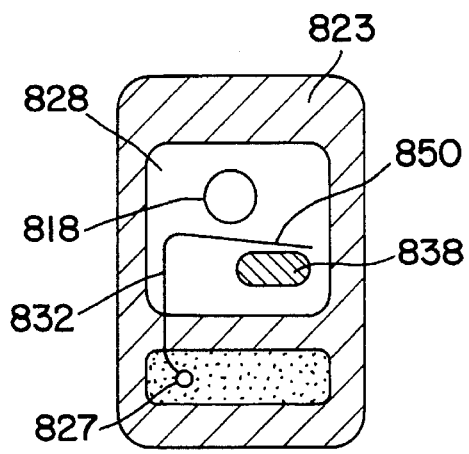
FIG. 8A and 8B show end sectional views, similar to FIG. 5 and FIG. 6, of a second embodiment of this invention.
Figure 8B:
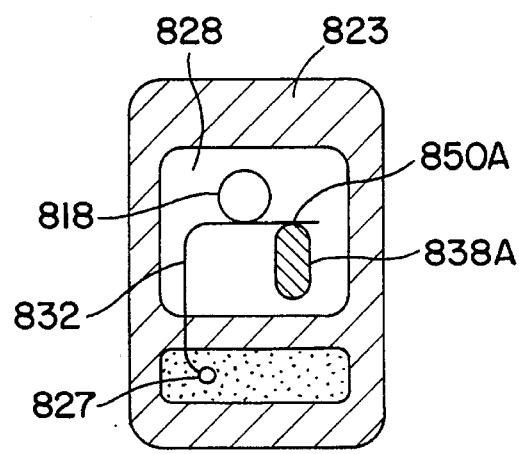

As further illustrations of embodiments included under the claims of the present invention, we refer to FIG. 8. FIG. 8A and FIG. 8B are sectional views, as is Section 5—5 in FIG. 4, through the connector blocks. In FIG. 8A, the connector block 823 represents a fixed and substantially closed housing in which there is a cavity 828. The cross-section of the elongated electrode array constituting the terminal mount is represented by the elements 818. The individual contacts for the second contact array associated with the connective housing is shown as the elements 832. In the FIG. 8A, the cross-section of the elongated cam shaft is indicated by the element 838, and it is in a position such that it does not contact the electrode contact 832, which is not in electrical connection with the terminal array contact 818. In addition, the connector contact 832 connects to the further connection wire means 827 as described above. Notice that there is gap between the cam shaft 832 in FIG. 8A and the point nearest to it 850 on the connector means contact 832.

In FIG. 8B, the cam shaft has been rotated by approximately 90° as illustrated by the element 838A. In this position, it has contacted the connector means contact 832 at the point 850A and in turn the connector contact 832 is in electrical connection with the terminal mount contact 818. This figure, therefore, illustrates that the cam shaft can be used to actively drive the second contact array associated with the connector housing towards the linear array or first array of contacts associated with the terminal mount. This is in contrast to the examples shown in FIGS. 1 through 7, where the connector mount contact arrays are spring-loaded, and normally in the inward position relative to the space or cavities in the housing, and the cam shaft serves in one orientation to spread them apart so as not to contact the terminal mount. This distinction indicates that the cam shaft or any equivalent actuation means can be used to drive the second contact array in the connector block or to release it, as the case may be, so as to contact the first contact array associated with the terminal mount.

Figure 9A:
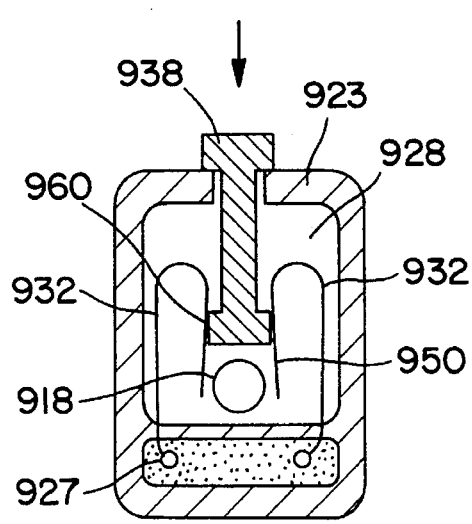
FIG. 9A and 9B show end sectional views, similar to FIG. 5 and FIG. 6, of a third embodiment of this invention.
Figure 9B:
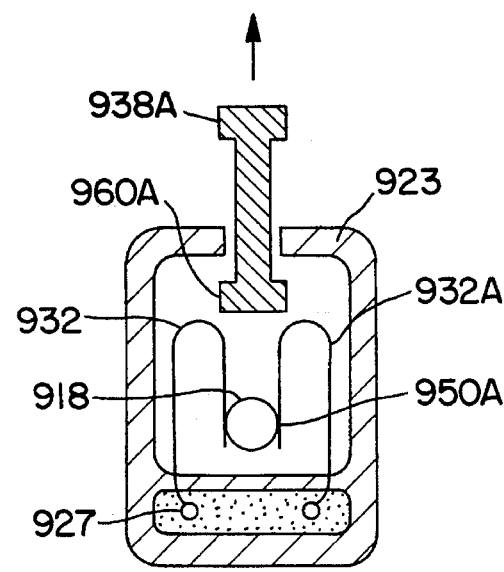

FIG. 9 shows a further embodiment of the present invention in which a plunger or other actuation means is used to move the second contact array associated with the connector block so as to make contact with the third contact array associated with the terminal mount. In FIG. 9A, an actuator means 938 takes the form of an elongated plunger or piston which moves into the elongated cavity or space 928 within the connector housing 923. In the position of FIG. 9A, there is a contact portion 960 of actuator means 938 which pushes apart the electrode contacts associated with the first contact array of the terminal mount, these contacts shown as a representative of sectional view of one by the number 932 and 932A. With the actuator means 938 in the "inward position," indicated by the arrow, it is more into the space and displaces the electrode contact 932 away from the first linear array elements 918 associated with the terminal mount. In this configuration of FIG. 9A, electrical contact, therefore, is not being made. However, in FIG. 9B, when the actuator element 938A is in the upward or outermost position, as shown by its position and arrow, then the actuator element 960A is no longer in contact with the electrode array elements of the second contact array 932, and, because of their spring-loaded nature, they then are free to move inward into a space further so as to contact the contact element of the first linear array associated with the terminal mount, indicated by the element 918. This is, therefore, yet another example of how an actuator element can be moved within the elongated cavity of the connector block or connector housing so as to move the second contact array elements into or away from contact with the first contact array elements associated with the terminal mount. We note that in both of these examples and the previous example, there was not particular need that the actuator element pass through the first contact array elements associated with, for example, 818 or 918 so as to effect the electrical contact of the first contact array elements with the terminal mount with the second contact array elements of the connector housing or connector mount.

The above described invention has been applied to devices used for monitoring electrical activity in epilepsy patients. This invention could apply equally well to electrodes use elsewhere in the body. For instance, it is well known that multiple contact electrodes are used in the cardiac mapping application and also for cardiac ablation procedures. Thus the connector design for multi-contact medical electrodes may be an invention applicable to the cardiac field also.

Additionally from the foregoing description, it will be understood that modifications can be made to the terminal mount 13 of the present invention and the connector assembly 23 thereof without departing from the teachings of the present invention.

It is understood that those skilled in the art can use the examples shown here and the claims associated with this invention to make modifications of the embodiments used as examples here. For example, various materials, configurations, shapes of electrode arrays, orientations of cam shafts, actuator means, etc. can be used. For instance, a linear actuator shaft could easily be used to be pushed longitudinally into the elongated length of the connector housing so as to affect the action and movement of the second contact array associated with the connector so as to make or break contact with the first contact array associated with the electrode terminal mount. Push pins of various types or squeeze mechanisms actuated from outside of the connector housings so as to push the actuator means and move it within the connector housing can easily be devised to also create an embodiment that is covered by the scope of the present claims.

Therefore, what we claim by U.S. Letters Patent are the following:

1. In a medical electrode having a plurality of tissue contact electrodes which has a plurality of separate lead wires for each of said tissue contact electrodes, and which lead from said tissue contact electrodes to a terminal mount, said terminal mount being connected to a connector means to make electrical connection with each of said lead wires, the improvement comprising:

a. said terminal mount having a first electrical contact array which comprises individual first electrical contact array electrical contacts which are individually connected to said lead wires and thus to said tissue contact electrodes; and;

b. said connector means comprising: a connector housing having a longitudinally extending space within it and, a second electrical contact array located within said space which comprises individual second electrical contact array electrical contacts;

an actuator means located within said space for controlling the position of the second electrical contact array electrical contacts relative to the first electrical contact array electrical contacts; said first electrical contact array being adapted to fit into said space, and said actuator means and said connector housing and said space being so adapted and cooperatively connected to said second electrical contact array that said actuator means can move with respect to said connector housing in such a way that when said first electrical contact array is fit into said space and said actuator means is moved with respect to said connector housing, said actuator means allows said second electrical contact array to move inwardly relative to said space, without acting through said first electrical contact array, and thereby allowing said second electrical contact array to contact said first electrical contact array without said actuator means being in physical contact with said second electrical contact array, whereby said first electrical contact array electrical contacts make individual electrical contact with said second electrical contact array electrical contacts, and thus said second electrical contact array electrical contacts make individual electrical connection with said tissue contact electrodes through said lead wires.

2. The apparatus of claim 1 wherein said space comprises an elongated cavity in said connector housing, said elongated cavity having communication with a region outside of said connector housing by a hole in said connector housing at one end of said elongated cavity, and said first electrical contact array comprises a sheathing with lead wires therein, and said first electrical contact array electrical contacts being a substantially linear electrical contact array of electrical contacts along said sheathing and whereby said linear electrical contact array can be inserted through said hole into said elongated cavity.

3. The apparatus of claim 2 wherein said second electrical contact array electrical contacts comprise flexible electrical contact arms which are arranged in a linear array within said elongated cavity, and said actuator means is an elongated cam shaft within said elongated cavity, said elongated cam shaft being moveable with respect to said elongated cavity by being rotatable substantially around the axis of said elongated cam shaft, such that in a first rotation position of said elongated cam shaft, said flexible electrical contact arms will move toward and electrically contact said first electrical contact array; and in a second rotation position of said elongated cam shaft, said flexible electrical contact arms will move away from and in a non-electrical contact position with respect to said first electrical contact array.

4. The apparatus of claim 3 wherein said elongated cam shaft is made from a substantially electrically insulative material, and said elongated cam shaft has an extension with an enlarged end which extends to the region outside of said connector housing, such that said elongated cam shaft can be rotated by finger force on said enlarged end so as to make or break said electrical connection between said first electrical contact array electrical contacts and said second electrical contact array electrical contacts.

* * * * *